US006814816B2

(12) United States Patent
Achar et al.

(10) Patent No.: US 6,814,816 B2
(45) Date of Patent: Nov. 9, 2004

(54) INDICATOR KIT

(75) Inventors: Sudhir Achar, Maharashtra (IN); Nimish Harshadrai Shah, Maharashtra (IN)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/678,559

(22) Filed: Oct. 3, 2003

(65) Prior Publication Data

US 2004/0065350 A1 Apr. 8, 2004

(30) Foreign Application Priority Data

Oct. 3, 2002 (IN) .................................. 863/MUM/2002

(51) Int. Cl.[7] .................................................. B08B 7/04
(52) U.S. Cl. ........................... 134/26; 134/27; 134/36; 134/42; 510/130; 436/56; 436/164; 436/169; 436/172
(58) Field of Search ......................... 436/56, 164, 169, 436/172; 134/26, 27, 36, 42; 510/130

(56) References Cited

U.S. PATENT DOCUMENTS

| 3,355,392 | A |   | 11/1967 | Cantor et al. ................. 252/99 |
| 3,650,831 | A |   | 3/1972  | Jungermann et al. ......... 134/27 |
| 4,858,465 | A | * | 8/1989  | Molina ......................... 73/104 |
| 4,965,063 | A |   | 10/1990 | Casey et al. ................. 424/7.1 |
| 5,225,675 | A | * | 7/1993  | O'Donnell .................... 250/302 |
| 5,504,014 | A | * | 4/1996  | Lindsay et al. .............. 436/501 |
| 5,572,319 | A | * | 11/1996 | Blackman et al. ........ 356/238.3 |
| 5,923,432 | A | * | 7/1999  | Kral ............................ 356/432 |
| 5,990,067 | A |   | 11/1999 | Franssen et al. ............ 510/240 |
| 2004/0065350 | A1 | * | 4/2004 | Archar et al. ................. 134/18 |

FOREIGN PATENT DOCUMENTS

| EP | 0886778 B1 | * | 6/2001 |
| JP | 61164158   | * | 7/1986 |
| JP | 06 034621  |   | 10/1994 |

OTHER PUBLICATIONS

PCT International Search Report for PCT/EP03/10945.*
UK Search Report No. GB 0305222.2 dated Jul. 16, 2003—1 page.
WPI Accession No. 1994–086319 abstract of JP 06–034621.

* cited by examiner

Primary Examiner—Sharidan Carrillo
(74) Attorney, Agent, or Firm—Alan A. Bornstein

(57) ABSTRACT

The invention provides method for the evaluation of washing or cleaning techniques on a substrate comprising:
  i. applying a selective indicator system on the substrate to be evaluated;
  ii. washing the substrate with water and/or detergent containing composition; and
  ii. contacting the washed surface with an indicator complimentary developer,
whereby inadequate washing is indicated when upon contacting of the developer it acts on the unwashed indicator to develop a colour indicative of the insufficient washing or cleaning.

4 Claims, 1 Drawing Sheet

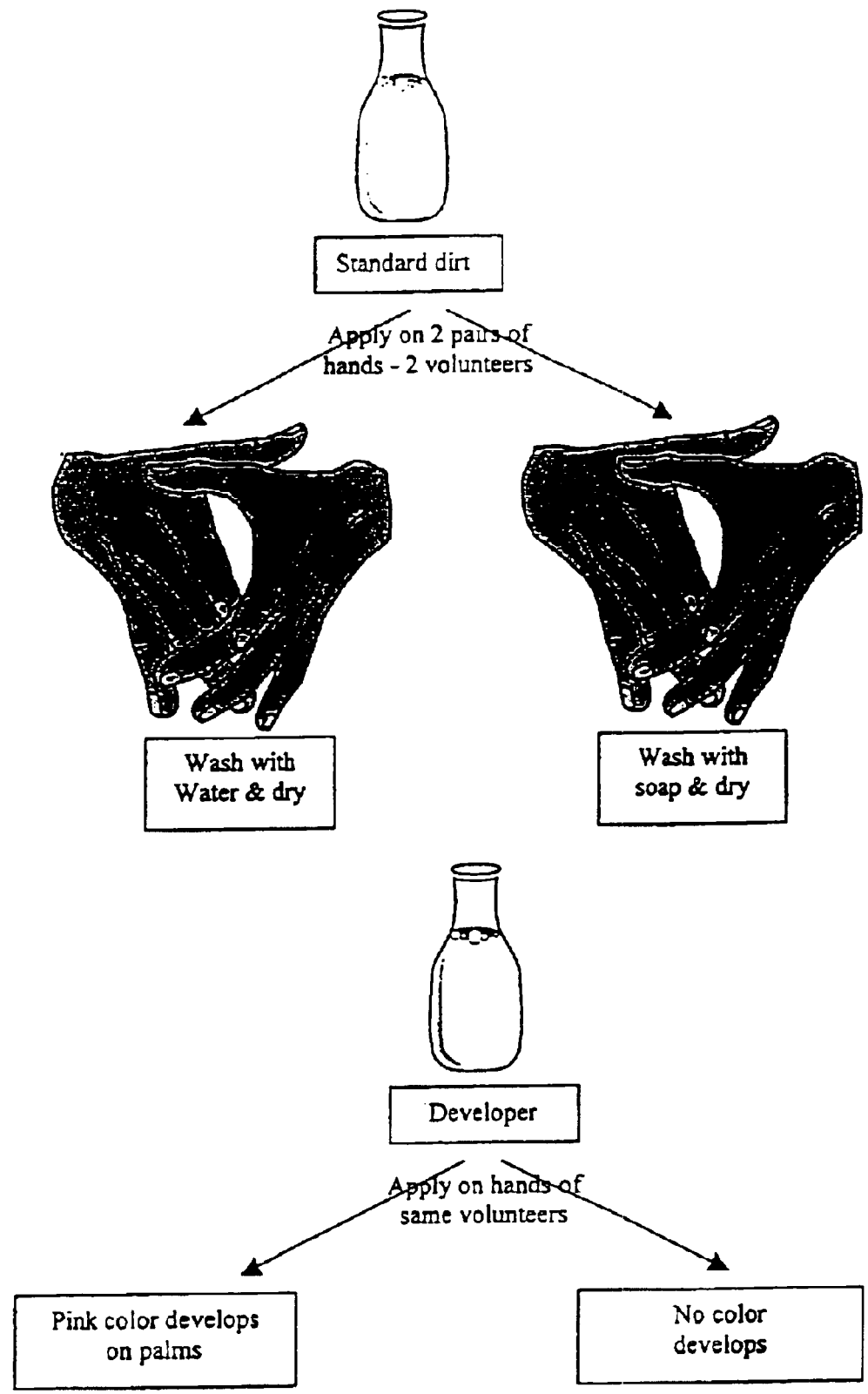

INDICATOR KIT

The present invention relates to a method for evaluating the effective cleaning/washing of substrates, and/or the deposition of desired actives/benefit agents on substrates such as oil based sunscreen agents as cosmetic compositions, and the like. The invention also relates to a kit adapted for simple and cost effective application of such method for evaluation of cleaning of substrates and/or deposition of actives/benefit agents on substrates.

U.S. Pat. No. 4,965,063 discloses a cleaning composition for surfaces containing a disappearing dye including a germicide, which facilitates indicating to the user effective delivery of the cleaning composition on the substrate. The dye is pH sensitive, such that upon exposure to air the dye disappears. In effect, the composition enables identification of the distribution of the cleaning composition on the substrate as soon as it is applied in the cleaning process, which however vanishes due to color changes. That is, the dye color changes as soon as the neutralization of the dye takes place on exposure to the atmospheric condition. In particular, the dye is selected such that it's color changes due to neutralization of the composition by the acidic $CO_2$ in the air, and the surface on which it is sprayed.

U.S. Pat. No. 33,555,392 discloses yet another alkaline germicidal cleaner with color indicator or an alkaline germicidal cleaning composition having indicator means to signify the minimum contact time for effective germicidal action in use dilution thereof. The cleaning composition disclosed includes selective dyes which can serve to provide a reliable indication to the user by change in it's colour that treatment of objects such as dentures, sickroom utensils, dishes, urinals and the like is continued for at least the interval required for complete germicidal effectiveness.

U.S. Pat. No. 3,650,831 discloses a method of removing deposits of soils from surfaces which comprises applying to the surfaces a caustic alkali including an acid base color indicator, and applying an aqueous solution which is sufficiently acidic to substantially neutralize the caustic and visibly change the color of the caustic. The purpose of this prior art had been to ensure that the messy to handle, sensitive and capable of injuring the user caustic alkali, which is usually used for cleaning surfaces for example interiors surfaces of oven and the like, after application for such cleaning is effectively removed from the substrate to avoid any such injury to the user and/or to ensure hygienic and safe further use of such device/substrate without problems of caustic contamination.

The above prior art goes to show knowledge in the art to provide modified cleaning compositions/disinfecting agents to ascertain either that the cleaning composition is maintained for the desired duration with the substrate for effective disinfecting/germicidal effects on substrates, or enable the user of such compositions to ascertain that the cleaning composition is effectively spread/applied on to the substrate desired to be treated/cleaned.

Personal hygiene involving cleaning/washing of hands and the like is of extreme importance to maintain proper health and avoid infections and the like. Thus, there is need to identify whether the washing/cleaning involving soaps/detergents and the like which one undertakes during regular washing/cleaning cycles provide for the desired cleanliness to meet desired standards of personal hygiene.

U.S. Pat. No. 5,990,067 discloses a method for ensuring personal hygiene following hand washing techniques by way of providing for a method of evaluating a person's hand wash technique. According to this method, invisible detection agents such as phosphorescent materials are used along with a soap or detergent based hand-washing medium used for washing/cleaning techniques. Thereafter, inspection of the hand/substrate after the washing/cleaning involving such soap/detergent with said detecting agent for any presence of the detection agent after washing is made. This would be indicative of lack of effective cleaning of the hand/substrate. For the purpose, the hand washing medium incorporating such detection agent is applied to the persons hands. Thereafter the hands are moved into contact with one another to spread the hand washing medium, both the hands are rinsed to remove the hand washing medium. Thereafter the hands are viewed in UV light for determination of the presence of any detecting agent to indicate an insufficient cleaning/washing technique.

The above U.S. '067 patent, whilst providing a method for evaluating a person hand washing technique, involves complexities in carrying out such method due to the required use of phosphorescent materials as a detection agent. Moreover, apart from this, the method further essentially requires a UV light source for determining the extent of the washing i.e. a UV light source to detect whether any amounts of the phosphorescent material residue remain after washing to indicate the non-effective coverage during the washing/cleaning of the hands. This, therefore, essentially has limited the application and use of the method of this art.

It is thus the basic object of the present invention to be able to provide for a method for evaluating the washing/cleaning techniques such as washing/cleaning of hands, and the like to ensure personal hygiene which would not involve the complexities of phosphorescent materials as well as any light source to carryout such method of evaluation.

Another object of the present invention is to be able to provide for a method for evaluating washing/cleaning techniques, which would involve simple steps and yet ensure effective cleaning/washing and thus favour maintaining desired personal hygiene.

Another object of the present invention is to be able to provide for a method for evaluating washing/cleaning techniques which can be carried out in any location where washing/cleaning activities are carried out by simple and cost effective steps/gadgets.

Another object of the present invention is directed to being able to provide a method for evaluation of deposition of benefit agent or substrate such as oil based sunscreen from cosmetic formulation and the like, which can be simply and readily carried out by the user thereby ensuring proper and effective deposition of such benefit agents.

Yet further object of the present invention is directed to being able to provide a kit adapted for use in such a method for evaluating effective washing/cleaning techniques, and/or deposition of agents in accordance with the present invention.

Thus according to a first aspect of the present invention there is provided a method for evaluation of washing/cleaning techniques on a substrate comprising:

i. applying to the substrate a selective indicator system on the substrate to be evaluated;
ii. washing the substrate with water and/or soap;
iii. contacting the thus washed surface with an indicator complimentary developer whereby adequate washing is indicated when the contacting of the developer fails to indicate any color change due to complete washing including the indicator while inadequate washing is indicated when upon contacting of the developer it acts on the unwashed indicator to develop a color indicative of the insufficient washing/cleaning.

According to a further aspect the method for evaluation of washing/cleaning comprise:

i. contacting the substrate to be washed/cleaned with selected oily material;
ii. further contacting the substrate with a selective indicator system;
iii. washing the substrate with water and/or detergent;
iv. contacting the thus washed surface with an indicator complimentary developer, whereby adequate washing is indicated when the contacting of the developer fails to indicate any color change due to complete washing including the indicator, whilst inadequate washing is indicated when upon contacting of the developer it acts on the unwashed indicator to develop a color indicative of insufficient washing/cleaning.

According to yet another aspect the method for evaluation of washing/cleaning comprises:

i. contacting the substrate to be washed/cleaned with oily material including a selective indicator system;
ii. washing the substrate with water and/or detergent;
iii. contacting the thus washed surface with an indicator complimentary developer, whereby adequate washing is indicated when the contacting of the developer fails to indicate any color change due to complete washing including the indicator, whilst inadequate washing is indicated when upon contacting of the developer it acts on the unwashed indicator to develop a color indicative of insufficient washing/cleaning.

According to yet another aspect of the invention there is provided a method for evaluating deposition of oily material such as benefit agents and the like on the substrate comprising:

i. applying the selected oily material based benefit agent and a selective indicator on the substrate to be covered, to obtain an benefit agent-indicator surface covering on said substrate;
ii. applying a selective indicator complimentary developer with or without washing, whereby a color change is visible on interaction of the developer with said indicator in the regions where benefit agent-indicator is duly deposited, and also indicated are any regions of the substrate with no such colour change left uncovered by the benefit agent-indicator application.

According to yet another aspect, the above method for evaluating deposition of oily material such as benefit agents and the like on substrate further comprises:

i. applying the said benefit agent-indicator in said regions of the substrate;
ii. washing the substrate in presence of the indicator and/or developer and evaluation of deposition.

In the above disclosed method of the invention the oil material can be any suitable oil material, but preferably silicone oils, vegetable oils and fats, mineral oils and fats, animal oils and fats, mineral oils, paraffin oils, petroleum, hydrocarbon and organic solvents, skin benefit agents, or sun screens e.g. Parsol MCX, or mixtures thereof.

The selected indicator means can be of any suitable color change based indicator preferably selected from phenolphthalein, methylene blue, resazurin, -3-5-triphenyl tetrazolium chloride (TTC).

The selected developer suitable for use in the method is dependent upon the indicator system used such that in case the indicator is phenolphthalein the developer can be an acid or a base depending upon whether the indicator is used in an acidic or a basic substrate. If Methylene Blue is used as an indicator a reducing agents can be used as a developer. Similarly, for Resazurin or 3-5-triphenyl tetrazolium chloride (TTC) a reducing agent can be used as a developer.

In the above method for evaluation of cleaning/washing following the evaluation is based on the change in color of the indicator system to identify whether the washing/cleaning is effective. The change in color to be monitored based on the selective indicator and developer is preferably as detailed under Table-I hereunder:

TABLE I

| No. | Selective Indicator System | Basis of Indication | Possible Selective Developer |
|---|---|---|---|
| 1 | Phenolphthalein | Acid/base-Colorless at acidic pH and pink color Post-neutralization. | Acid-base |
| 2 | Methylene Blue | Redox-colorless in oxidised state-blue in reduced form. | Reducing agent is a developer |
| 3 | Resazurin | Redox-colorless in oxidised state-red in reduced form | Reducing agent is a developer |
| 4 | -3-5-triphenyl tetrazolium chloride | Redox-colorless in oxidised form red insoluble in reduced form | Reducing agent is a developer |

As would be evident from the above, the method involves the use of indicator and the oil on the substrate to be evaluated. For the purpose, the ratio of indicator to oil is selected preferably in the range of 0.01% to 50% more preferably 0.5% to 25% and most preferably 1% to 5%.

According to a further aspect of the invention there is provided a kit for use in the above method for evaluation of the cleaning/washing and/or deposition of benefit agents comprising;

i. an indictor system adapted for application on the substrate to be evaluated;
ii. a selective developer complimentary with said indicator to indicate color changes on interaction with the indicator;
iii. an instruction manual comprising the method steps for such evaluation of the cleaning/washing deposition of the benefit agent.

According to another aspect the kit of the invention comprising:

i. an indictor including an oil material adapted for application on the substrate to be evaluated;
ii. a selective developer complimentary with said indicator to indicate color changes on interaction with the indicator;
iii. an instruction manual comprising the method steps for such evaluation of the cleaning/washing/deposition of benefit agent.

According to yet another aspect the kit of the invention comprises:

i. at least one oil material for application on the substrate;
ii. at least one indictor system adapted for application on the substrate to be evaluated;
iii. at least one selective developer complimentary with said indicator to indicate color changes on interaction with the indicator;

iv. an instruction manual comprising the method steps for such evaluation of the cleaning/washing/depositions of benefit agents.

According to yet another aspect of the invention there is provided a kit for use in the above method of evaluation of the cleaning/washing of the invention comprising:

i. at least one indictor adapted for application on the substrate to be evaluated;
ii. at least one selective developer complimentary with said indicator to indicate color changes on interaction with the indicator;
iii. at least one wash/cosmetic formulation;
iv. an instruction manual comprising the method steps for such evaluation of the cleaning/washing/depositions of benefit agents.

EXAMPLES

The nature of the invention its objects and advantages are explained hereunder in greater detail in relation to non-limiting exemplary embodiments hereunder and also with reference to the accompanying figures.

Example-I

The method for evaluation of the wash/cleaning in accordance with the present invention was carried out as described hereunder.

Material Used

Parsol MCX (oil)
Polyacrylic acid
Phenolphthalein (Indicator)
Water,
0.1N NaOH solution in water (Developer)

The method followed

Standard dirt was applied on hands of two volunteers.

Both the volunteers were required to apply approximately 12 ml of an indicator system. The indicator solution was prepared by dispersing 3 g of Parsol MCX (oil), 2 g polyacrylic acid and 0.25 g phenolphthalein in 94.75 ml of water using a Silverson high-speed stirrer to obtain a stable microemulsion.

One of the two volunteers was then required to wash the hands with only water and dry the same. The other volunteer was required to wash the hand with water and soap and thereafter dry the same.

Both the volunteers were then required to apply the developer on the hands using a cotton swab.

Findings

It was found that the volunteer who washed the dirt only with plain water without use of the soap had substantially retained the oily indicator system including the dirt in hand, and as soon as the developer was applied pink color developed on contact with the indicator. On the other hand, the volunteer who washed with soap had the oily indicator system along with the dirt completely removed and the developer when applied did not indicate any color change since the indicator system was not retained on the hands. The method of evaluation is further illustrated in accompanying FIG. 1.

It would be apparent from the above that the indicator and developer combination used in the method of the invention provides for means for evaluation of the extent of removal of oils and dirt from hands during washing cycles.

Applying the same methodology it is also possible to ascertain whether oil based actives such as sunscreens etc. are effectively and uniformly distributed on substrate on application. In such case, the oily benefit agent can be applied together with the indicator system. Subsequently, the application of the developer would indicate the extent of deposition of cosmetic/benefit agent on the substrate.

Similarly, the principle could be applied to determine cleaning efficiency of oily soils from fabric surfaces.

It is thus possible by way of present invention to provide for a simple and ready to use method for evaluating the cleaning/washing and the effectiveness in such cleaning/wash procedures especially for personal hygiene. Importantly, the use of readily available indicator and complimentary developer provides for simple and cost effective method of evaluation of the extent of cleaning/washing or deposition of benefit agents as the case may be following the method of invention. Added to the above, the possible availability of the kit comprising the selected indicator, developer with or without the wash/cosmetic formulation and the instruction manual make the method easily applicable and can generate consciousness of the desired hygiene in personal washing and cleaning.

Importantly, considering the requirement of cleanliness in maintaining good health and avoiding infectious diseases, the method and kit of the invention would serve not only for assessment of washing/cleanliness achieved but even ensure that during the cleaning and washing cycles the cleaning attended is proper and free of harmful contamination/microbes.

What is claimed is:

1. A method of evaluating the cleanliness of a person's hands comprising the steps of:

a) applying a selective indicator to a person's hands, wherein said selective indicator changes color upon interaction with an indicator complimentary developer;
   b) washing both hands with water and/or a detergent containing composition;
   c) contacting both hands with said indicator complimentary developer; and
   d) determining inadequate washing of a person's hands by visually detecting the presence of a color change resulting from the interaction of said selective indicator with said indicator complementary developer, wherein the detection of the presence of the color change does not require a UV light source.

2. A method according to claim 1, additionally comprising contacting the person's hands with a selected oily material prior to applying said selective indicator.

3. A method according to claim 1, wherein a selected oily material is included with said selective indicator.

4. A method according to claim 1, wherein steps (b) and (c) are performed simultaneously.

* * * * *